United States Patent [19]

Riley, Jr.

[11] Patent Number: 5,055,303

[45] Date of Patent: Oct. 8, 1991

[54] SOLID CONTROLLED RELEASE BIOADHERENT EMULSIONS

[75] Inventor: Thomas C. Riley, Jr., St. Louis, Mo.

[73] Assignee: KV Pharmaceutical Company, St. Louis, Mo.

[21] Appl. No.: 304,124

[22] Filed: Jan. 31, 1989

[51] Int. Cl.$^5$ ............................................... A61K 9/02
[52] U.S. Cl. .................................... 424/436; 514/966; 514/967
[58] Field of Search ................. 424/436; 514/966, 967

[56] References Cited

U.S. PATENT DOCUMENTS

| | | | |
|---|---|---|---|
| 4,439,194 | 3/1984 | Harwood et al. | 424/436 |
| 4,551,148 | 11/1985 | Riley, Jr. et al. | 424/DIG. 14 |
| 4,698,359 | 10/1987 | Niederer et al. | 514/966 |
| 4,891,208 | 1/1990 | Janoff et al. | 424/450 |

Primary Examiner—Thurman K. Page
Assistant Examiner—Amy Hulina
Attorney, Agent, or Firm—Roper & Quigg

[57] ABSTRACT

Solid delivery systems which at body temperature exhibit controlled release and bioadherence characteristics. These systems are emulsions which are water in oil in nature and whose internal phase is greater than that of the external phase. That is, the internal phase comprises at least 60% of the system.

10 Claims, No Drawings

SOLID CONTROLLED RELEASE BIOADHERENT EMULSIONS

BACKGROUND OF THE INVENTION

I. Field of the Invention

The present invention is directed to solid delivery systems which at body temperature exhibit controlled release and bioadherence characteristics. Specifically, the invention is concerned with solid delivery systems that are formed from and whose internal phase is greater than that of the external phase which are water in oil in nature.

II. Description of the Prior Art

High internal phase ratio emulsions, those whose internal phase is greater than 70%, have been discovered to exhibit bioadherent properties. Such emulsions are described in U.S. Pat. No. 4,551,148. It generally is known that such systems are thixotropic liquids or semisolids. The emulsions in their most viscous state resemble an ointment or cream.

Under certain circumstances it is preferable to deliver active agents through a solid which melts at body temperature. However, it is generally recognized that water should be avoided in the formulation of these solids. Reasons for the avoiding of water in such systems are well known and are discussed in *The Theory and Practice of Industrial Pharmacy*, Lachman et al, 1976, page 264 and Senior, Rectal Administration of Drugs, *Advances in Pharmaceutical Sciences*, edited by Beckett et al, Vol. 4, 1974, page 367. Conventional systems do not include more than 20% water when long term stability is required and usually about 10%. Formulations have been produced with as much as 40% water but such products demonstrate only short term stability.

It is an object of the invention to provide a system which comprises a high or internal phase ratio emulsion, at least 60% internal phase, in a solid form that at body temperature exhibits controlled release and bioadherent characteristics. It is a further object of the invention to provide a drug delivery system which does not draw moisture from tissues. Finally, it is an object of the invention to provide a delivery system which does not leak from the body orifice.

SUMMARY OF THE INVENTION

A solid drug delivery system whose lipoidal phase melts at body temperature. The system comprises an emulsion whose internal phase is nonlipoidal and is at least 60% of the emulsion.

DESCRIPTION OF THE PREFERRED EMBODIMENTS

The present invention is directed to a delivery system which is a solid but melts at body temperature. In particular the system is comprised of an emulsion which has been solidified by the use of such traditional components as the hard fats, waxes, fatty alcohols and acids and fatty acid esters. The systems contain at least 60% by volume and preferably 70% by volume of water or other nonlipoidal media. The systems may incorporate an active agent which is approved for or used for the treatment, prophylaxis, cure or mitigation of disease; for aesthetic or cosmetic usage; for diagnostic purposes; or for systemic drug therapy. Examples of such active agents include:

| | |
|---|---|
| nonsteroidal antiinflamatory e.g. | acemetacin |
| polypeptides | spermicides |
| antibodies | anti fungals |
| glycoproteins | antacids |
| antihypertensives | antiulcer agents |
| coronary dialators | cough/cold preparations |
| mucousides | |

The systems are characterized by the controlled release of an active substance from the delivery system following the melting of the system at a receptor site, site of action, site of absorption or site of use. The systems can also be characterized as being bioadherent and as not demonstrating offensive leakage from the body orifice. Since the systems are solid at room temperature, they can be easily inserted into body orifices or administered orally. Thus, the systems of the invention combine the advantages of a solid whose external phase melts to form a nonthixotropic cream at body temperature.

The emulsion's internal phase contains at least a portion of the active agent and is nonlipoidal. The nonlipoidal character of the phase renders it miscible with water. Preferably the internal phase comprises water, glycerine, or combinations thereof. Generally, it is desirable that the internal phase be of high osmotic pressure. The internal phase may be multiphasic and may be a solution, suspension, emulsion or combination thereof and it contains at least a portion of the active agent. Also, the internal phase may contain suspended solids, penetration enhancers, emulsions, osmotic enhancers, extenders and diluants, as well as fragrances, colors, flavors and buffers.

The emulsions have an external phase. This phase is lipoidal and is the continuous phase of the systems. The term lipoidal pertains to any of a group of organic compounds comprising the neutral fats, fatty acids, waxes, phosphatides, petrolatum, fatty acid esters of monoprotic alcohols and mineral oils having the following common properties: insoluble in water, soluble in alcohol, ether, chloroform or other fat solvents, and which exhibit a greasy feel. Examples of oils suitable for use in these delivery systems are mineral oils with viscosities of 5.6 to 68.7 centistokes, preferably 25 to 65 centistokes, and vegetable oils illustrated by coconut, palm kernel, cocoa butter, cottonseed, peanut, olive, palm, sunflower seed, sesame, corn, safflower rape seed, soybean and fractionated liquid triglycerides of short chain (naturally derived) fatty acids. This external phase may also contain fragrances, colors, flavors, and buffers.

The emulsions contain emulsifiers. Preferably, the emulsifiers are soluble in the lipoidal or external phase. Suitable emulsifiers are those oil miscible surface active compounds which are acceptable for use in foods, pharmaceuticals, and/or cosmetics Examples of such emulsifiers are low molecular weight polyglycerols which have been esterfied with fatty acids or fatty acid esters, or mono and diglyceride mixtures alone or with the addition of metallic soaps, such as, aluminum stearate. The metallic soaps appear to improve the characteristics of some of the emulsions.

The overall degree of hardness, tack and melting point is controlled primarily by the blending of the external phase components, and to a lesser degree by the amount of dissolved species in the internal phase. A certain degree of plasticity is also required in the external phase, otherwise the finished product will crack and weep rather easily. Plasticity is usually achieved by incorporating appropriate amounts of lipid-soluble oils and liquid surfactants. The main types of ingredients used to control the overall melting point and hardness are the hard fats (mostly triglycerides, but some mono and diglycerides), waxes (paraffin, microcrystalline, vegetable, mineral and animal), fatty alcohols and acids and fatty acid esters. These techniques are well known in the formulating of solids that melt at body temperature.

The systems may be prepared by continuous or batch processes. As in preparing conventional emulsions, shear force is applied to the system components by use of homogenizers, mills, impingement surfaces, ultrasound, shaking or vibration. Unlike conventional emulsions, the mixing shear should be at low levels in order to prevent destruction of the system by imparting excess energy. Since these systems are solid at room temperature, they must be made with both the internal and external phases at a temperature approximately 5 degrees-10 degrees above the melting point of the highest melting component in the system. It is also desirable to package the material while still in the hot, semi-solid stage in order to avoid significant water loss. This will usually mean filling directly into a preformed package and then sealing. Filling directly into an open mold allows too much loss of water.

The systems may be prepared by mixing the internal with the external phase in a planetary-type mixer. Another manner of preparing the system is by use of a continuous mixer which comprises multiple impellers. The external phase is first introduced into the continuous mixer until it reaches the level of the lowest impeller in the mixing chamber. The two phases are then simultaneously introduced through the bottom of the mixer in proper proportion as its impeller or impellers rotate to apply a shear to the components. The finished product emerges through the top of the mixer. The actual speed of the impeller or impellers will vary, depending upon the product produced as will the rate of flow of the two phase streams.

The following example is illustrative of the invention:

Method of Preparation: The active agent, and ingredients of the internal phase were mixed together at an elevated temperature. (approximately 55 degrees C.) The ingredients of the external phase were mixed together in a one-gallon steam jacketed vessel. The internal phase composition was slowly added to the external phase composition as the two phases were mixed together with a split disc stirrer at low shear until the desired viscosity was obtained. The product was then filled into a preform package.

EXAMPLES

| Ingredients | % W/W |
|---|---|
| Purified Water | 73.5 |
| Glycerin | 1.0 |
| Sodium Carboxymethylcellulose | 0.5 |
| Theophylline | 4.0 |
| Glyceryl esters of mixtures of saturated vegetable fatty acids | 11.0 |
| Microcrystalline wax | 7.0 |
| Sorbitan tristearate | 3.0 |
| | 100.0 |

A second example is as follows:

| 8% Miconazole Nitrate Suppository | Wt. % |
|---|---|
| Purified Water | 66.36 |
| Miconazole Nitrate | 8.0 |
| Triglyceride Suppository Base (Melt point 42 degrees C.) | 5.0 |
| Triglyceride Suppository Base (Melt point 34 degrees C.) | 4.75 |
| Triglyceride Suppository Base (Melt point 34 degrees C.) | 4.75 |
| Mineral Oil | 4.0 |
| Sorbitan Diisosterate | 3.0 |
| Sorbitan Tristearate | 3.0 |
| Methylparaben | 0.11 |
| Propylparaben | 0.03 |
| Microcrystalline Wax | 1.0 |
| | 100.0% |

These solid delivery systems are unlike conventional emulsions and those described in U.S. Pat. No. 4,551,148. They are bioadherent and exhibit controlled release properties. They are not thixotropic. Upon melting at body temperature they become creams and not liquids. This characteristic is important in achieving bioadherence and controlled release.

The system is not rigid but is moldable when hand pressure is applied. For instance, if a suppository of the invention is placed in a warmer at 37 degrees C., after 15-30 minutes it still maintains its form. However, if a shearing force is applied it will flow like a cream due to a decrease in viscosity.

The invention may be embodied in other specific forms without departing from the spirit or essential characteristics thereof. The present embodiments are therefore to be considered in all respects as illustrative and not restrictive, the scope of the invention being indicated by the appended claims rather than by the meaning and range of equivalency of the claims are therefore intended to be embraced therein.

I claim:

1. A bioadherent controlled release drug delivery system which is a solid at room temperature and a cream at body temperature, which comprises: a solid emulsion system containing a continuous lipoidal external phase, an active agent, and a nonlipoidal internal phase that is at least 60% by volume of the emulsion, wherein said internal phase is selected from the group consisting of water, glycerine, and mixtures thereof.

2. The delivery system of claim 1 wherein said system contains plasticizers.

3. The delivery system of claim 1 wherein said internal phase is at least 70% by volume of the system.

4. The delivery system of claim 1 wherein said system is a suppository.

5. The delivery system of claim 1 wherein said system is orally administered.

6. The delivery system of claim 1 wherein the external phase melts to form the cream.

7. A method for preparing a bioadherent controlled release drug delivery system, which comprises:
  a) mixing an active pharmaceutical agent with a nonlipoidal internal phase selected from the group consisting of water, glycerine, and mixtures thereof until a homogeneous mixture is obtained;
  b) mixing the homogeneous mixture with a continuous lipoidal external phase at low shear to obtain a uniform emulsion system, wherein the temperatures of the internal phase and external phase are about 5 degrees to about 10 degrees above the melting point of the highest melting point component in the system and the nonlipoidal internal phase is at least 60% by volume of the emulsion system; and c) inserting the product into preformed molds and recovering a bioadherent controlled release drug delivery system which is a solid at room temperature and a cream at body temperature.

8. The process of claim 7 wherein the internal phase is slowly added to the external phase while mixing the system.

9. The process of claim 7 wherein the nonlipoidal internal phase is at least 70% by volume of the internal phase.

10. The process of claim 7 wherein the preformed mold is a preformed package.

* * * * *